United States Patent
Dufour et al.

(10) Patent No.: US 11,540,811 B2
(45) Date of Patent: Jan. 3, 2023

(54) ULTRASOUND SYSTEM AND METHOD FOR CORRECTING MOTION-INDUCED MISALIGNMENT IN IMAGE FUSION

(71) Applicant: KONINKLIJKE PHILIPS N.V., Eindhoven (NL)

(72) Inventors: Cecile Dufour, Suresnes (FR); Thomas Shu Yin Tang, Ontario (CA); Gary Cheng-How Ng, Redmond, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 92 days.

(21) Appl. No.: 16/959,534

(22) PCT Filed: Jan. 4, 2019

(86) PCT No.: PCT/EP2019/050143
§ 371 (c)(1),
(2) Date: Jul. 1, 2020

(87) PCT Pub. No.: WO2019/134959
PCT Pub. Date: Jul. 11, 2019

(65) Prior Publication Data
US 2021/0068790 A1    Mar. 11, 2021

(30) Foreign Application Priority Data
Jan. 4, 2018  (EP) ..................... 18305004

(51) Int. Cl.
*A61B 8/00*   (2006.01)
*A61B 8/08*   (2006.01)
(52) U.S. Cl.
CPC .......... *A61B 8/5207* (2013.01); *A61B 8/4254* (2013.01); *A61B 8/4416* (2013.01);
(Continued)

(58) Field of Classification Search
CPC ... A61B 8/5207; A61B 8/4254; A61B 8/4416; A61B 8/466; A61B 8/483; A61B 8/5276
See application file for complete search history.

(56) References Cited

U.S. PATENT DOCUMENTS 6,312,382 B1 * 11/2001 Mucci ..................... A61B 8/02
                                                  600/437
6,443,896 B1    9/2002 Detmer
(Continued)

FOREIGN PATENT DOCUMENTS

CN    103230283 A    8/2013
EP    3056151 A1     8/2016
(Continued)

OTHER PUBLICATIONS

PCT/EP2019/050143 ISR & WO, dated Mar. 21, 2019, 13 Page Document.

(Continued)

*Primary Examiner* — Amanda Lauritzen Moher
*Assistant Examiner* — Brooke Lyn Klein

(57) ABSTRACT

The present disclosure describes ultrasound imaging systems and methods, which may enable the automatic identification of an image plane in a pre-operative volume corresponding to a real-time image of a moving region of interest. An example method includes receiving real-time ultrasound image data from a probe associated with a position-tracking sensor, generating real-time images based on the real-time ultrasound data and deriving a motion model from the real-time ultrasound image data. The method may further include automatically identifying an image plane in a pre-operative data set to correspond to the real-time ultrasound image by correcting for motion-induced misalignment between the real-time data and the pre-operative data.

13 Claims, 14 Drawing Sheets

(52) U.S. Cl.
CPC .............. *A61B 8/466* (2013.01); *A61B 8/483* (2013.01); *A61B 8/5261* (2013.01); *A61B 8/5276* (2013.01)

(56) References Cited

U.S. PATENT DOCUMENTS

| | | | |
|---|---|---|---|
| 6,530,885 | B1 | 3/2003 | Entrekin |
| 2005/0215904 | A1* | 9/2005 | Sumanaweera ........ A61B 8/481 600/458 |
| 2011/0028843 | A1 | 2/2011 | Hyun et al. |
| 2011/0245673 | A1* | 10/2011 | Kamiyama ......... G01S 7/52071 600/443 |
| 2012/0116229 | A1* | 5/2012 | Miyachi ............... A61B 8/0891 600/463 |
| 2013/0279780 | A1 | 10/2013 | Grbic et al. |
| 2014/0193053 | A1* | 7/2014 | Kadoury ................ G06T 15/08 382/131 |
| 2014/0235998 | A1* | 8/2014 | Kim ..................... A61B 5/0035 600/424 |
| 2014/0243671 | A1* | 8/2014 | Holl ..................... A61B 8/4209 600/443 |
| 2014/0316247 | A1* | 10/2014 | Hwang ................ A61B 6/5247 600/437 |
| 2015/0238169 | A1* | 8/2015 | Mizukami ........... A61B 8/5223 600/449 |
| 2016/0174945 | A1* | 6/2016 | Oh ....................... A61B 8/4405 382/131 |
| 2017/0065257 | A1* | 3/2017 | Nakamura ........... A61B 8/0883 |

FOREIGN PATENT DOCUMENTS

| | | |
|---|---|---|
| WO | 2006059668 A1 | 6/2006 |
| WO | 2016169759 A1 | 10/2016 |
| WO | 2017046674 A1 | 3/2017 |
| WO | 2017109685 A1 | 6/2017 |

OTHER PUBLICATIONS

Yang et al: "Subject-Specific Real-Time Respiratory Liver Motion Compensation Method for Ultrasound-MRI/CT Fusion Imaging"; Int J Cars, Published Online Jun. 14, 2014, Springer Publishing, 13 Page Document.

* cited by examiner

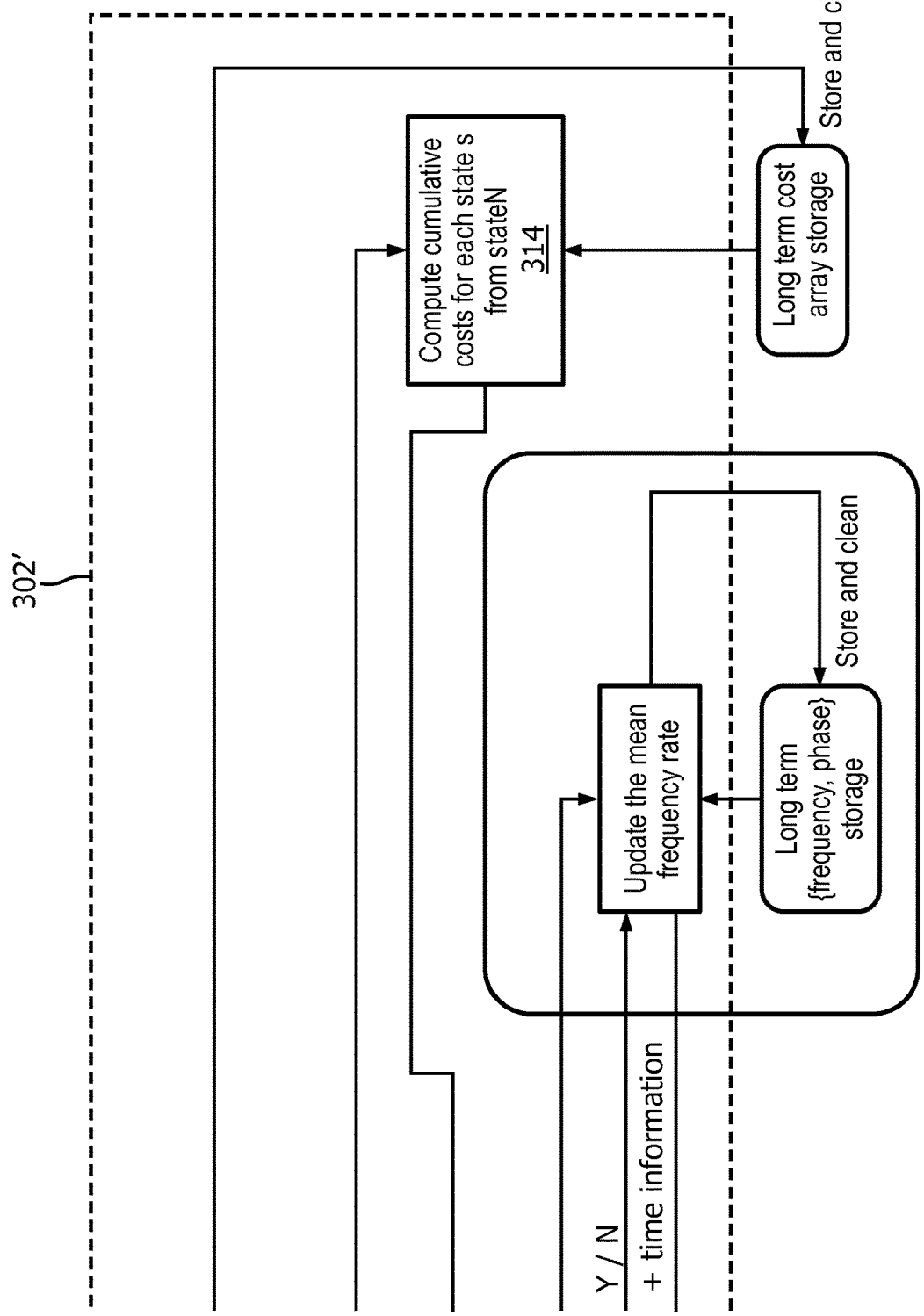

ULTRASOUND SYSTEM AND METHOD FOR CORRECTING MOTION-INDUCED MISALIGNMENT IN IMAGE FUSION

CROSS-REFERENCE TO PRIOR APPLICATIONS

This application is the U.S. National Phase application under 35 U.S.C. § 371 of International Application No. PCT/EP2019/050143, filed on Jan. 4, 2019, which claims the benefit of European Patent Application No. 18305004.6, filed on Jan. 4, 2018. These applications are hereby incorporated by reference herein.

TECHNICAL FIELD

The present disclosure relates generally to ultrasound systems and methods for correcting motion-induced misalignment when performing image fusion, for example when fusing real-time images (e.g., during real time ultrasound) and pre-operative images (e.g., obtained using a different imaging modality such as magnetic resonance (MR) or computed tomography (CT), or pre-operative 3D ultrasound (US) data).

BACKGROUND

Fusion of live ultrasound image of a patient with a pre-operative 3D volume of the same patient but from another modality (usually, but not limited to, MR or CT) requires spatial calibration. For that purpose ultrasound probes are typically equipped with position tracking (e.g., electromagnetic (EM) tracking) sensors. One such medical imaging system is described in U.S. Patent Application Publication No. 2011/028843 A1. In order to spatially align the images from the two modalities, the tracking system is first calibrated. The calibration step provides a rigid transformation between the live ultrasound data and the pre-operative data set such that spatial synchronization can be automatically maintained. However, even if the calibration step is performed very accurately, the fused image may be subject to misalignment error in real-time tracking conditions due to motion of the patient, for example due to respiratory or cardiac motion. To reduce such fusion error, the "default" pre-operative 2D plane to be used for the fusion (as indicated by the EM tracker) may be replaced by another plane P representative of a different respiratory state. However, to do so, multiple data sets of pre-operative data associated with different respiratory state would need to be available to apply this solution. It is more often the case that only a single set of pre-operative data is available. Thus, it more often necessary to select an alternative plane P from the single available pre-operative data set, and existing systems vary in the way in which they identify this alternative plane P to be used. For example, in one known system, the live ultrasound images and pre-operative CT images are aligned via image processing performed on the live and CT images so as to match features in the two sets of image data. Another known system uses an additional respiratory tracking system with a sensor positioned on the patient's chest to derive a model for correcting the respiratory-induced misalignment.

EP 3056151 A1 relates to a method for fusing at least one ultrasound image and a pre-stored modality image, such as a CT or MR image. The ultrasound fusion imaging method includes a selection step, a registration step, and a fusion step. The selection step is for selecting at least one ultrasound image from at least one previously stored piece of ultrasound video data, including an ultrasound image obtained by acquiring a target object in at least one plane, and position indicating information corresponding to each ultrasound image. The position information is generated by a position sensor fixed to the ultrasonic probe. The registration step is for registering the selected at least one ultrasound image with a modality image, using the location of the position indicating information of the at least one ultrasound image. The fusion step is for fusing the registered ultrasound image with the modality image.

WO 2017/109685 A1 discloses a medical imaging apparatus for inspecting a volume of a subject. The medical imaging apparatus comprises an ultrasound acquisition unit, including an ultrasound probe for acquiring ultrasound image data of the subject, an image interface for receiving medical image data of the subject, and a position determining unit for determining a position of the ultrasound probe. An alignment unit is provided for aligning the ultrasound image data and the medical image data based on anatomical features of the subject and the detected position of the ultrasound probe, and for adapting the alignment of the ultrasound image data and the medical image data based on a motion model. The motion model is defined based on the position of the ultrasound probe, and the variation of the repetitive patterns of the common anatomical features throughout the plurality of ultrasound images. An image processing unit is provided for processing the ultrasound image data, and the medical image data to fuse the ultrasound image data, and the medical image data based on the alignment to combined image data.

However, currently known solutions may not be as robust as may be desired, for example because they are either dependent on the image quality of both pre-operative and live ultrasound data, because they rely on image features such as diaphragm position, which may not always be discriminant for a good match, nor even present in the image, depending on the probe orientation towards an anatomical structure of interest (e.g. liver), and because in some cases they require additional hardware (e.g., respiratory movement tracker) and introduce additional complexity to the system. Alternative methods for correcting for motion misalignment may thus be desirable.

SUMMARY

Examples in accordance with the present disclosure may provide an improved systems and methods for correcting motion-induced misalignment when performing image fusion.

An ultrasound imaging system according to principles of the present disclosure may include or be operatively associated with an ultrasound probe for imaging a subject in real time and with a position-tracking sensor connected to the probe. The system may include a processor communicatively coupled to the ultrasound probe and to a source of previously-acquired image data, the previously-acquired image data comprising a 3D dataset corresponding to an imaged volume of the subject. The processor may be configured to receive real-time ultrasound image data and generate a real-time ultrasound image (e.g., a 2D or a 3D image) based on a current image frame from the real-time ultrasound data. The processor may be further configured to derive a motion model from the real-time ultrasound image data and resynchronize the motion model to movement of an anatomical feature of the subject (e.g., automatically or responsive to user input). The processor may be further configured to identify a motion-corrected image plane in the imaged volume based on position information from the position-tracking sensor and the motion model for generating a motion-compensated pre-operative image, and to fuse the real-time ultrasound image with the motion-compensated pre-operative image to produce a combined image.

A method according to principles of the present invention may include receiving real-time ultrasound image data responsive to ultrasound transmitted by a probe toward a subject, wherein the probe is associated with a position-tracking sensor and generate a real-time ultrasound image based on a current image frame from the real-time ultrasound data. The method may further include deriving a motion model from the real-time ultrasound image data, resynchronizing the motion model to movement of an anatomical feature of the subject, accessing a previously-acquired image data set corresponding to an imaged volume of the subject, identifying a motion-corrected image plane of the imaged volume based on position information from the position-tracking sensor and the motion model for generating a motion-compensated pre-operative image, and fusing the real-time ultrasound image with the motion-compensated pre-operative image to produce a combined image.

Any features or preferred embodiments described herein with regard to the method of the invention may also be applied to the ultrasound imaging system of the invention.

In accordance with principles of the present invention, no respiratory movement tracker is used in either of the ultrasound imaging system or the method, i.e. the motion model is derived without using data from a respiratory movement tracker. This reduces the hardware complexity of the inventive system and method.

Further, in accordance with principles of the present invention, the motion-corrected image plane in the imaged volume is identified purely based on position information from the position-tracking sensor and the motion model. Thus, preferably no registration or alignment e.g. based on the alignment of anatomical features between the real-time ultrasound image and the pre-operative image data set is carried out, and thereby, the invention is independent of the image quality of the real-time ultrasound image and the pre-operative image data and thus very robust.

According to a preferred embodiment, the processor may be configured to generate long term correlation (LTC) data for each of a plurality of incoming frames of real-time ultrasound image data; and determine the cycle frequency and the phase associated with each incoming frame by identifying at least two local minima of a LTC curve corresponding to the LTC data associated with each incoming frame. As described by equation (1) below, a LTC curve is generated by subtracting the incoming frame from each of the previous frames (or vice versa) and summing the result of the subtraction over all pixels. Preferably, the previous frames from at least the previous one or two cycles are used to compute the LTC curve. Accordingly, the LTC curve for this incoming frame will have a minimum at a time in the past when the subject was last in the same breathing position, which will be one cycle length ago, but there may also be a minimum in between, namely when the subject is currently in an intermediate breathing position, i.e. one that is passed twice in each breathing cycle. Thus, information about the cycle frequency and the phase of the motion may be derived from the LTC curve.

DETAILED DESCRIPTION

Figure 1:
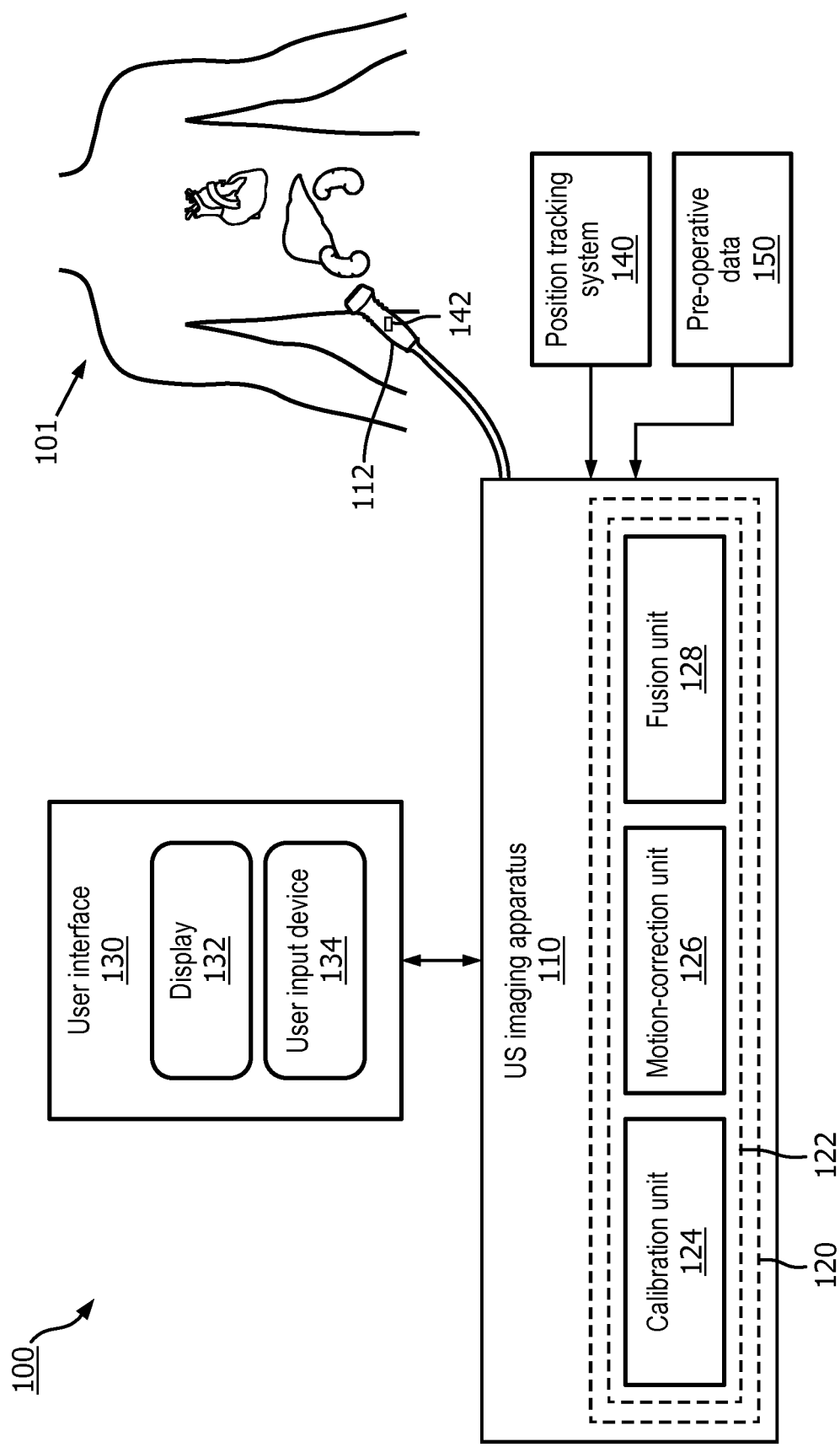
FIG. 1 shows a block diagram of an ultrasound imaging system in accordance with embodiments of the present disclosure.

The following description of certain exemplary embodiments is merely exemplary in nature and is in no way intended to limit the disclosure or its applications or uses. In the following detailed description of embodiments of the present systems and methods, reference is made to the accompanying drawings which form a part hereof, and in which are shown by way of illustration specific embodiments in which the described systems and methods may be practiced. These embodiments are described in sufficient detail to enable those skilled in the art to practice the presently disclosed systems and methods, and it is to be understood that other embodiments may be utilized and that structural and logical changes may be made without departing from the spirit and scope of the present system. Moreover, for the purpose of clarity, detailed descriptions of certain features will not be discussed when they would be apparent to those with skill in the art so as not to obscure the description of the present system. The following detailed description is therefore not to be taken in a limiting sense, and the scope of the present system is defined only by the appended claims.

In accordance with principles of the present invention, an ultrasound imaging system may be communicatively connected to a source of real-time ultrasound image data (e.g., an ultrasound probe) and to a source of previously acquired image data (interchangeably referred to herein as pre-operative data). For example, the system may include or be operatively connected to an ultrasound probe for acquiring ultrasound image data in real time. The ultrasound imaging system may also be connected to a source of pre-operative data, e.g., a data storage device such as a picture archiving and communication system (PACS) server. The pre-operative data may be a 3D dataset corresponding to an imaged volume of the subject, which may have been acquired using any imaging modality, for example CT, MRI, PET, or 3D US. The system may further include or be operatively associated with a position-tracking system. For example, the probe may be equipped with a position-tracking sensor, such as an electromagnetic (EM) sensor or other type of sensor, a field generator, and a processor configured to determine the position of the probe in 3D space. The system may also include a calibration unit (which may also be referred to as registration unit), which is configured to maintain alignment or registration between the real-time ultrasound images and the pre-operative data such that fused images including ultrasound image data and pre-operative data can be displayed in real-time to the user. As will be described further with reference to the figures, the system may include a motion correction unit, which may enable the system to automatically identify a different (a motion-adjusted or motion-compensated) candidate image plane from the pre-operative data for fusion with the real-time data than would otherwise be selected purely based on the position information from position-tracking system.

FIG. 1 shows an illustration of a system 100 according to some embodiments of the present disclosure. The system 100 includes a medical imaging device (e.g., an ultrasound imaging apparatus 110) which is operatively (i.e., communicatively, such as via a wired or wireless communication link) connected to a probe 112. The probe 112 may be used to image a volume (e.g., anatomic structures such as the liver, heart, kidney, or potions thereof) of a subject 101. The volume to be imaged may include a region of interest (e.g., an anatomical site or structure of interest, such as a liver, heart, kidney, or any other tissue or organ). In the illustrated example, the probe 112 is an ultrasound probe comprising an array of transducer elements operable to transmit ultrasound waves toward the volume to be imaged and further operable to detect echoes responsive to the transmitted ultrasound. The transducer elements may be arranged in a 1D or 2D array. The ultrasound probe 112 may be used to obtain real-time ultrasound image data. The real-time ultrasound image data can be used to generate real-time ultrasound images (also referred to as live ultrasound images). The terms real-time and live are used generally to describe image data acquisition and display of images occurring during the acquisition of the image data as opposed to post acquisition display and evaluation of images generated from previously acquired image data.

The imaging apparatus 110 may include a control unit 120 connected to the ultrasound probe 112 for controlling the acquisition of ultrasound data, e.g., for providing beam steering and/or beam forming functions. The control unit 120 may include a processing unit 122, which is operable to generate ultrasound images based on the detected echoes. The processor 122 is further configured to receive pre-operative data, automatically spatially register the incoming live ultrasound images to the pre-operative data, and to further adjust the spatial registration to compensate for motion-induced misalignment prior to fusing the image data of the two data sets (i.e., real-time and pre-operative data).

The imaging apparatus 110 may also include a memory, which may be configured to store, among other things, image data such as the real-time ultrasound image data, and/or processor-executable instructions for configuring the processor to perform functions associated with spatial registration and image fusion. As described, the processor 122 may be configured (e.g., responsive to processor-executable instructions stored in memory) to automatically spatially register the live ultrasound image to the pre-operative data, e.g., to extract a corresponding slice from the pre-operative 3D dataset. This spatial registration, in accordance with some embodiments, may involve motion correction. Motion correction may be performed by applying a motion model to the pre-operative data to identify an alternative slice in the pre-operative data (different than a default slice selected based solely on position data), which alternative slice better corresponds to the live image after motion-induced misalignment has been accounted for by the motion model.

The imaging apparatus 110 is communicatively connected to a source of pre-operative data 150, for example a storage device (e.g., a PACS server) or another medical imaging apparatus (e.g., a MRI scanner, a CT scanner, an ultrasound scanner, or any other apparatus using any type of imaging modality or any combination thereof). The pre-operative data may be a 3D data set of medical image data, which may be obtained by any imaging modality. In some embodiments, the pre-operative data may be obtained by a different imaging modality than ultrasound, for example it may be a 3D dataset obtained by computed tomography (CT), magnetic resonance imaging (MRI), or a positron-emission tomography (PET), also referred to as a CT volume, an MRI volume, a PET volume, respectively, or the pre-operative data may be a previously acquired ultrasound data, e.g., a 3D US dataset (or an US volume) obtained from the same patient. The pre-operative data, as the name implies, is obtained prior to the real-time imaging (e.g., the live ultrasound imaging, which may occur during an invasive procedure such as a biopsy). Thus, the pre-operative data may be interchangeably referred to herein as previously acquired image data. In the illustrated example, the processor 122 includes a calibration module 124 for spatially registering the live images to the pre-operative data, a motion-correction unit 126 for adjusting the spatial registration to account for motion-induced misalignment, and a fusion unit 128 operable to fuse the motion-compensated pre-operative image with the live ultrasound image to produce a combined image. The imaging apparatus 110 is operatively associated with a user interface 130, which includes a display unit 132, e.g., for displaying the combined images in real-time. The user interface may also include a user input device 134 for receiving user input, e.g., for controlling the image acquisition process. The input device 134 may include, for example and without limitation, a keyboard, a mouse, a trackball, one or more buttons provided on a control panel, and/or one or more soft controls provided on a touch sensitive display.

The imaging apparatus 110 is operatively associated with a position tracking system 140 (e.g., an electromagnetic tracking (EM), optical or other type of position tracking system). The position tracking system 140 may include a position tracking sensor 142 (e.g., an EM sensor) attached to the probe and a processor configured to determine the position of the sensor 142 and thus the probe with reference to a 3D coordinate system. For example, the position tracking system may relate the spatial position of an EM sensor and thus the probe to a coordinate system of an EM tracking field generator. The calibration unit 124 may then register or correlate the coordinate system of the tracking field generator to a coordinate system of the pre-operative image data, thus enabling spatial registration between the pre-operative image data and the live ultrasound data. In this manner, the position of the ultrasound probe 112 can be used to identify a corresponding image plane within the pre-operative volume. In some examples, the function of this processor may be performed by the calibration unit 124 or generally be implemented within the processor 122 of the imaging apparatus 110.

A fusion unit 128 may be used to fuse the live image with the pre-operative image to produce a combined image for display. The live image may be overlayed with the pre-operative image, or alternatively the images may be displayed side-by-side, to produce the fused or combined image. However, as described, image registration or alignment, which is based only on the position tracking information may not account for motion-induced misalignment which may in turn reduce the quality of the image fusion process. Thus, the processor 122 may be further configured, as described herein, with additional functionality to account for and correct for such motion-induced misalignment.

Figure 5:
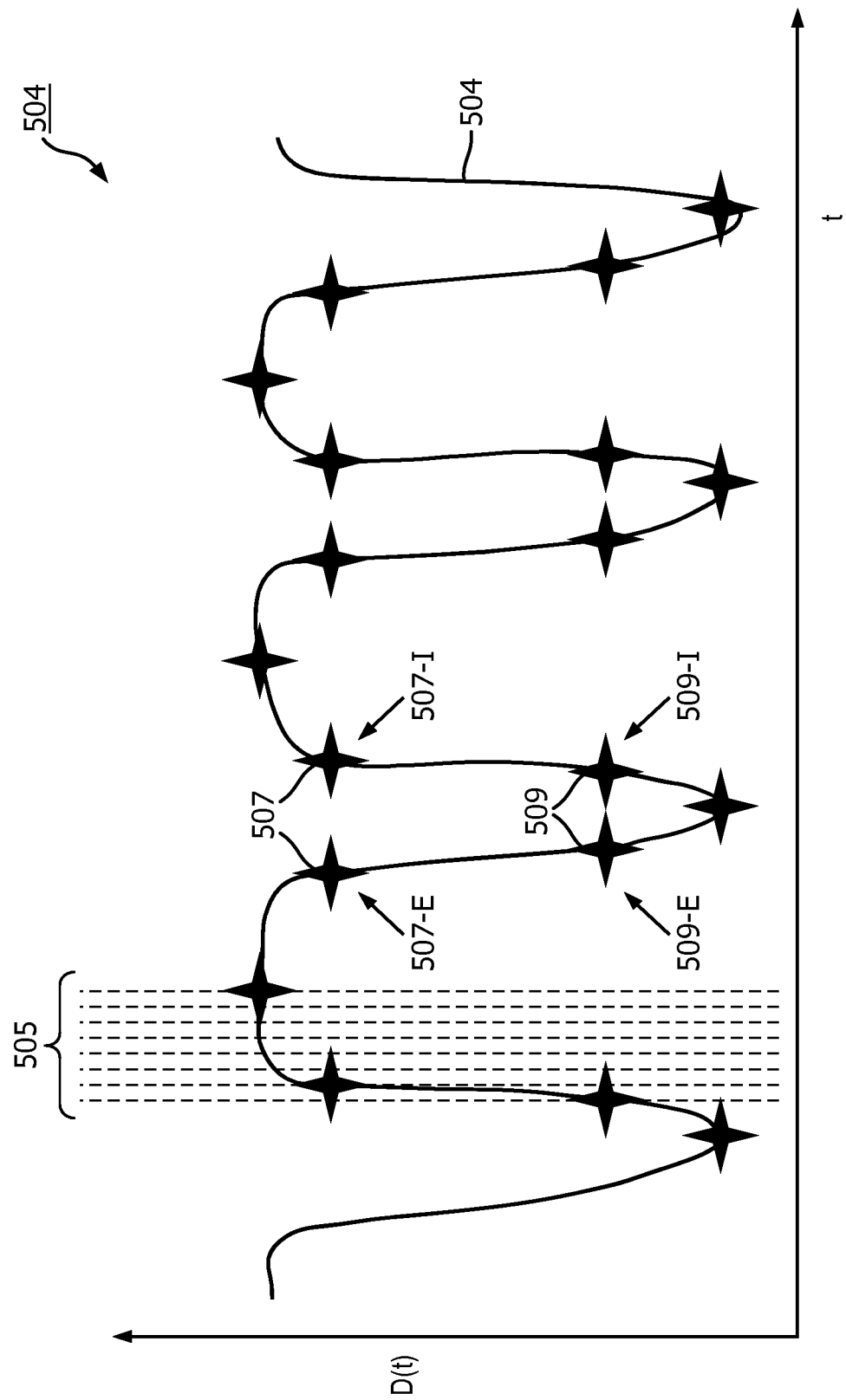
FIG. 5 shows an example respiratory-induced motion model for a liver as derived from real-time ultrasound data in accordance with principles of the present disclosure.

According to embodiments of the present disclosure, the processor 122 may include a motion-correction unit 126. The motion correction unit 126 may utilize a motion model to correct for any motion-induced misalignment between the live ultrasound image and the pre-operative data. The motion model may be a mathematical model (e.g., a mathematical representation, for example as shown in FIG. 5) of the motion trajectory of an anatomical feature of interest within the imaged volume. In some embodiments, the motion model may be derived based on image data including only ultrasound image data and specifically from the real-time ultrasound data. That is, unlike existing solutions in which images from both the ultrasound and preoperative (e.g., CT data) are image processed to match features in the images and thus facilitate alignment, the current motion model does not rely on the pre-operative data. Instead, and for example in the context of respiratory-induced motion, real-time ultrasound data is acquired for a temporal window that is greater than one breathing cycle of the subject, and the breathing cycle parameters are extracted solely from the real-time ultrasound image data. Image processing can be performed on the real-time ultrasound data, in some examples, to identify repeating features or patterns within the acquired frames such that the phase, rate and/or amplitude of motion can be determined. The phase, rate, and amplitude of motion can then be used to select an alternate image plane (other than the default or purely position-based image plane) from the pre-operative data set. In this manner, the motion-correction unit enables more precise alignment or registration of the live image to a corresponding image plane in the pre-operative image data even if the anatomical feature of interest is in motion, e.g., due to vital movements of the subject such as respiration. In some embodiment, such as when imaging the liver, the motion may be seen as being generally in the cranio-caudal direction and thus, the motion model may also be referred to as a cranio-caudal motion model.

Figure 2:
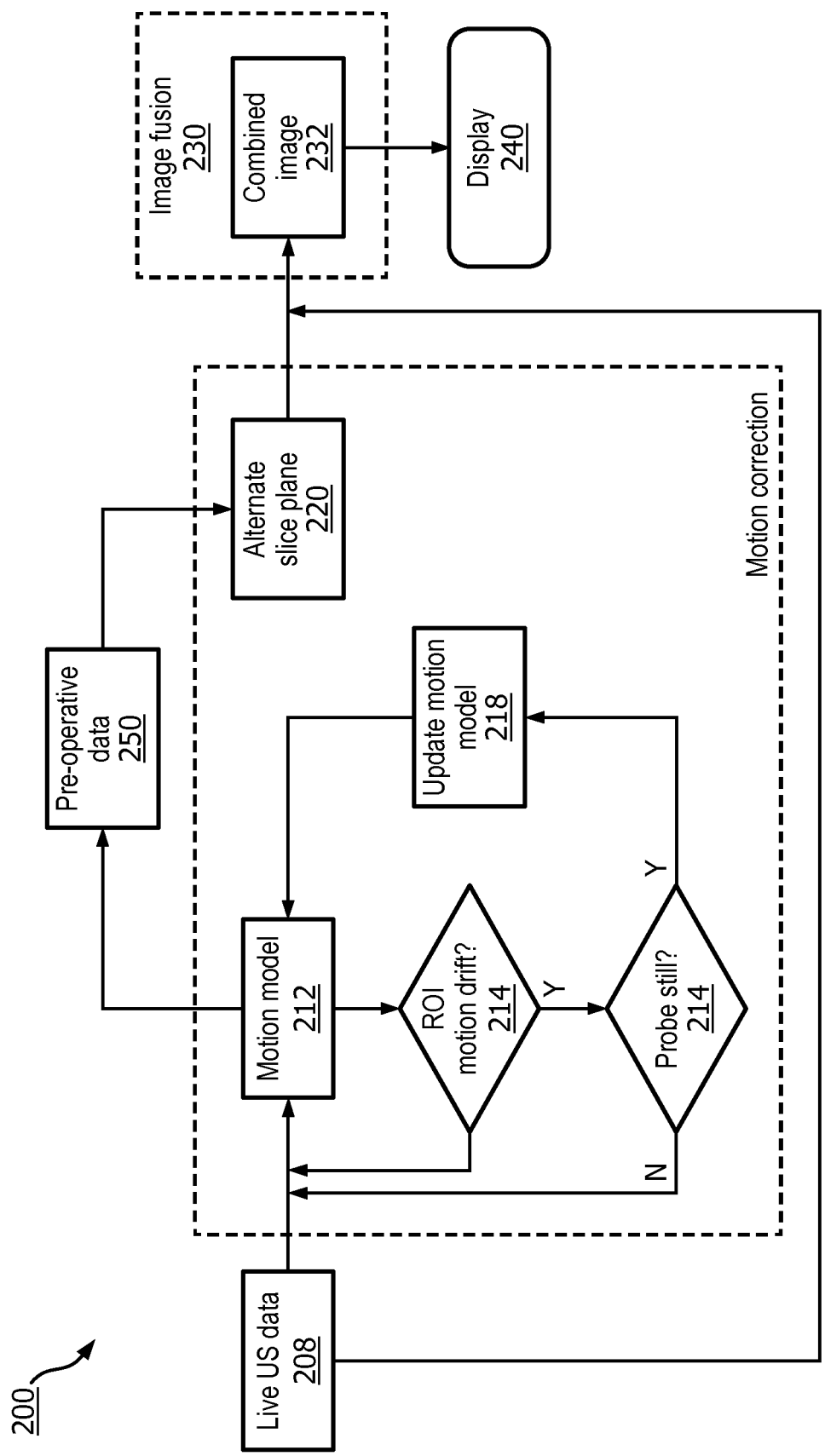
FIG. 2 shows processing components of an ultrasound imaging apparatus in accordance with principles of the present disclosure.

FIG. 2 shows a functional block diagram of a processor 200 of an ultrasound imaging system according to the present disclosure. The processor 200 may be used to implement the motion correction unit 126 in FIG. 1. In this example, the processor 200 is configured to receive live or real-time ultrasound data, as shown in block 208, and apply a motion model 212 to a pre-operative data set 250 to extract a motion-corrected image plane (as shown in block 220) from the pre-operative set for generating motion-corrected (or motion-compensated) pre-operative image that corresponds to the live image. The motion-corrected pre-operative image and the live image are then combined by the image fusion unit 230 to produce a combined image 232 for display on display unit 240.

As shown in FIG. 2, the processor 200 is communicatively coupled to a source of real-time ultrasound data (e.g., an ultrasound probe) and to a source of pre-operative data. The processor 200 may be configured to derive a motion model 212 based, in part, on imaging data which includes only ultrasound data (e.g., without reference to any other type of medical imaging data), and preferably without reference to respiratory movement tracking data. In some embodiments, the processor 200 may be configured to derive the motion model 212 further based on user inputs. For example, in the case of simple periodic respiratory-induced motion, the motion of certain anatomical structures (e.g., the liver) may be characterized as simple periodic motion in the cranio-caudal direction and the motion model 212 may thus be a cranio-caudal model, i.e. an estimate of a respiratory-induced motion of an anatomical feature along a cranio-caudal direction of the subject as a function of time, defined based on breathing rate, phase, and amplitude of the respiratory cycle. Such motion model assumes that the motion remains steady; however, in reality the patient's breathing may change and thus one or more parameters (e.g., breathing rate, phase, and/or amplitude) of the respiratory cycle may fall out of synch with the motion model. Accordingly, in some examples, the processor may be further configured to dynamically update the motion model to account for any perturbation in the motion (as shown in block 214) and to thereby maintain synchrony between the motion as estimated by the motion model and the actual motion of the anatomical feature (e.g., the patient's liver). The term dynamically implies that the processor may be configured to continuously automatically update the motion model (e.g., at each incoming frame or after sever new frames) to maintain synchrony between the motion model and the organ motion. In some examples, the resynchronization of the model may be performed responsive to user input, e.g., responsive to receiving an indication to initiate synchronization.

Additionally, in some examples, the processor 200 may be configured to monitor or detect movement of the probe. For example, the processor 200 may be configured to determine if the probe is stationary (as shown in block 216), e.g., based on the position-tracking data. When the probe is determined to be stationary, the processor 200 may proceed with updating (e.g., as shown in block 218) or synchronization of the motion model to the actual motion of the anatomy. However, if the probe is determined not to be stationary (e.g., probe movement exceeding a given threshold is detected), the processor 200 may pause synchronization and use the version of the motion model last updated prior to probe movement being detected. In the latter situation, the motion-corrected registration or alignment of live and pre-operative images continues but based on a static version of the motion model rather than a dynamically updating motion model, until probe movement ceases and the processor 200 resumes motion model synchronization. Additionally to motion estimation and/or correction, the processor 200, alone or in combination with other processors of the medical imaging apparatus, may be further configured to perform other functions of the medical imaging apparatus, e.g., functions for producing the ultrasound images based on the real time data and/or for producing images based on the pre-operative data.

Figure 3:
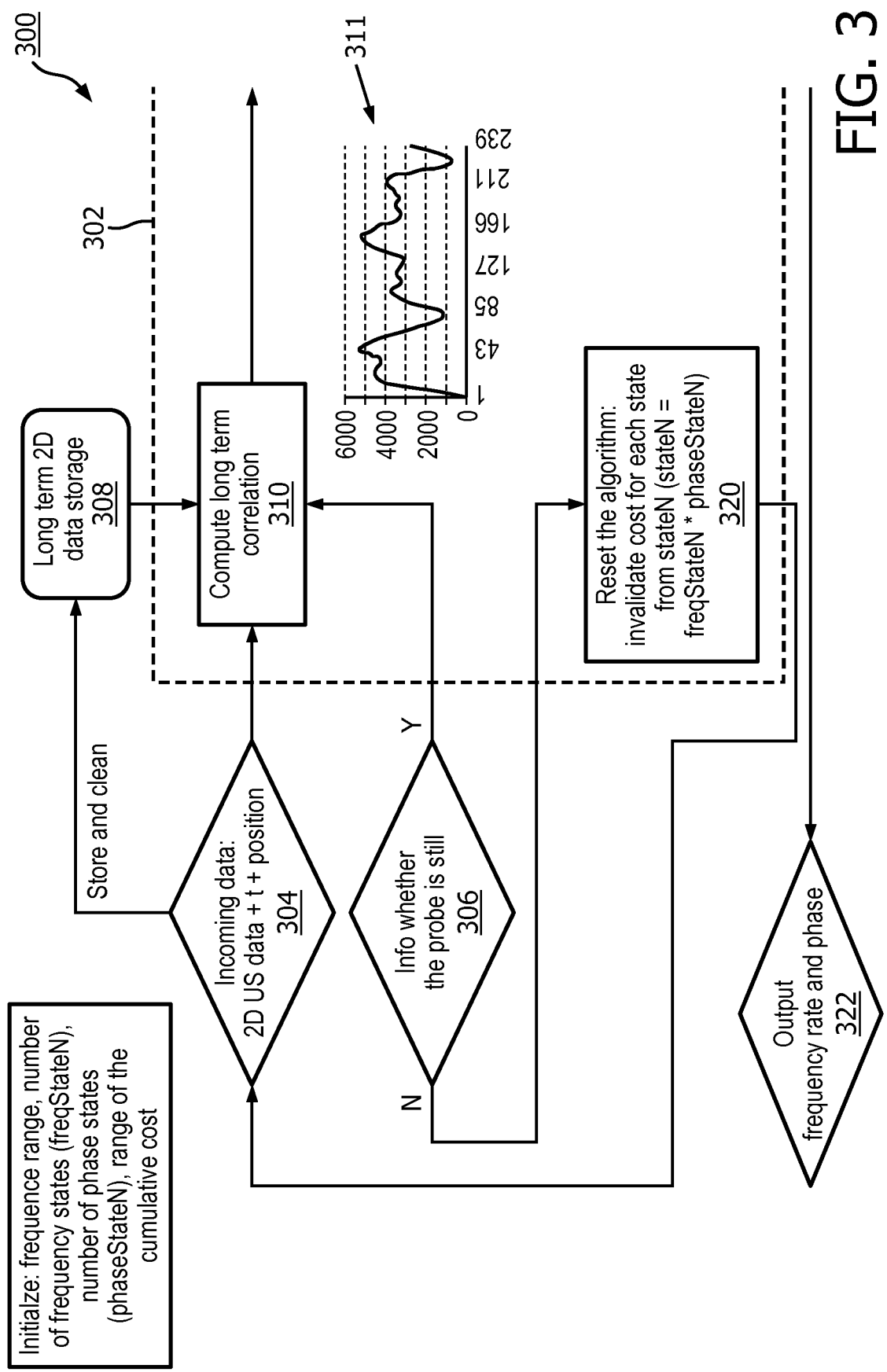
FIG. 3 shows a functional block diagram of an algorithm for correcting motion-induced misalignment when performing image fusion between real time and pre-operative data in accordance with principles of the present disclosure.
Figure 3:
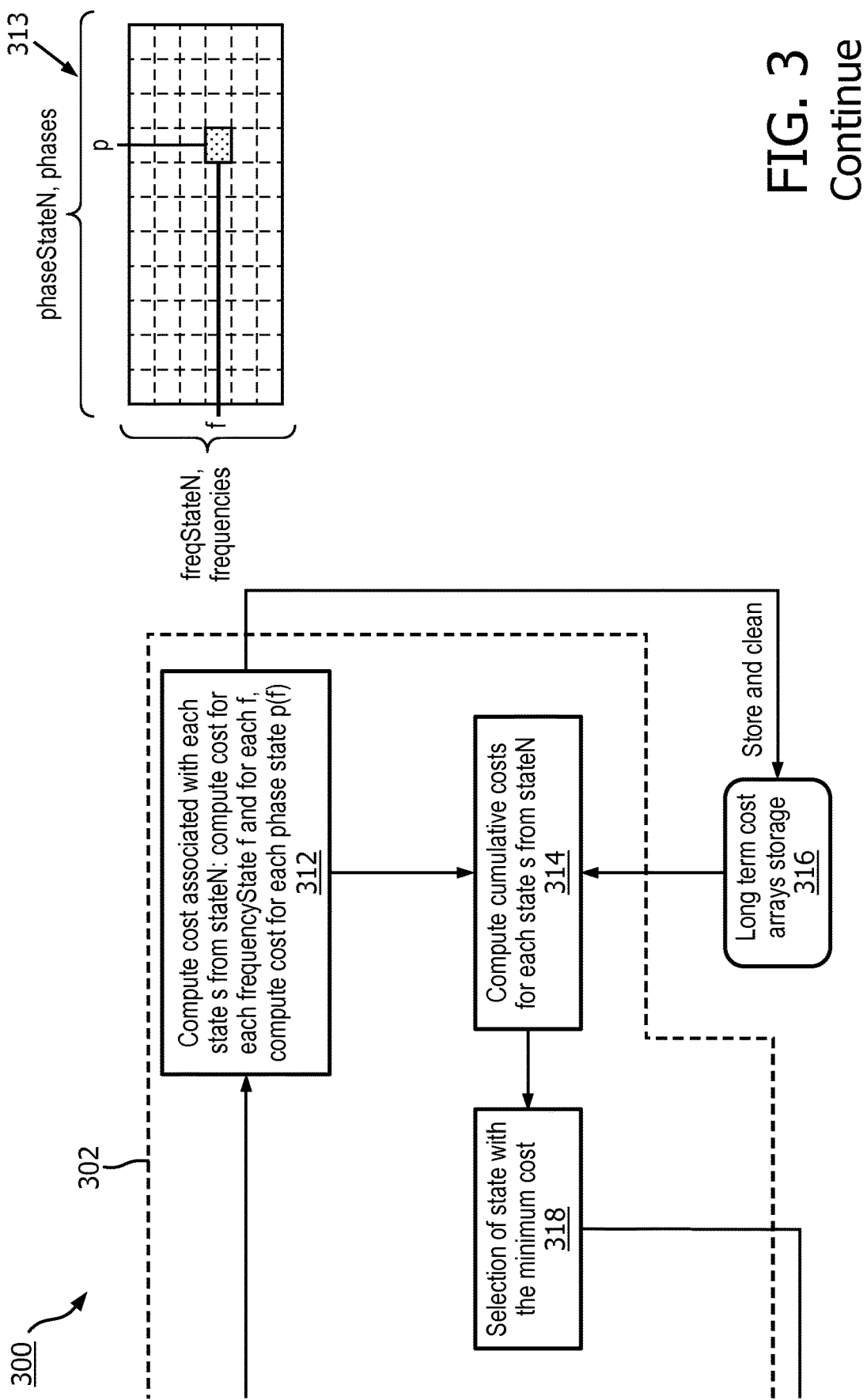

FIG. 3 shows a functional block diagram of an example algorithm or process 300 for spatial registration with motion-correction, which may be implemented (in hardware and/or software) in a processor of a medical imaging apparatus, such as the ultrasound imaging apparatus 110. The example algorithm in FIG. 3 is based on long term correlations computed on successive frames or a portions thereof (also referred to as image frames) over an amount of time greater than one motion cycle (e.g., one respiratory cycle). The embodiment in FIG. 3 will be described with reference to respiratory-induced motion. However, the principles described may be applicable to other type of motion. The algorithm or process 300 takes advantage of repetitive patterns that may be found among images through a motion cycle. For example, and referring also to FIG. 5, which shows a liver motion model 504 as represented by trajectory or displacement curve 504 derived according to embodiments of the present disclosure, it can be observed that the positions of anatomical features during the inhalation phase may be very similar to those during the exhalation phase. D(t) or d(t) indicates the displacement d as a function of time. As an example, the position of feature 507 on inhalation 507-I is similar to the position of feature 507 on exhalation 507-E, and similarly, the positions of feature 509 on inhalation and exhalation, 509-I and 509-E respectively, are similar. Thus, by analyzing a series of temporally successive frames 505 (e.g., by computing long term correlation among frames or by performing motion estimation), parameters defining the periodic respiratory motion can be extracted from the ultrasound data alone and thus a motion model can be defined as a function of time based on the parameters extracted from the ultrasound data.

Referring back to FIG. 3, upon initiation of the algorithm or process 300 certain parameters of the algorithm are initialized, such as the frequency range, the number of frequency states (freqStateN), number of phase states (phaseStateN), and the range of the cumulative cost. In the case of respiratory motion, a realistic respiratory cycle may be between 3 and 5 seconds for an adult and between 2 and 3 seconds for a child. The frequency range may initialize at a default frequency range, for example about 12 to 20 cycles per minute for an adult or about 20 to 30 cycles per minute for a child, which may be determined at least in part based on patient age information as input by the user, e.g., prior to initiating live ultrasound. In some examples, the frequency range may be adjustable responsive to user input, e.g., after defaulting to the pre-programmed range or the system may require the range to be input by the user. Similarly, the number of frequency and phase states may default to a given value, for example, 32 frequency states and 64 phase states. These numbers are purely illustrative and other number (smaller or greater than the specific examples) of states may be used, which may be pre-programmed and/or adjustable by the user. For example, the number of phase states may be optimized to improve visual quality (e.g., visual jerkiness may result from an undersampled respiratory cycle).

Once initiated, the phase is automatically updated by the algorithm, taking timing information into account, leading to the selection of a new plane of the pre-operative 3D volume for each incoming live US image. Additionally, in some instances, whenever a perturbation or a drift occurs in the pace of the anatomical structure motion, resynchronization is performed.

The process begins as block 304 with the algorithm receiving a plurality of frames of real-time image data and timing information. The frames may also be coupled to long term storage 308 to free up buffer space for new incoming frames. For each incoming frame, the processor 302 may generate long term correlation (LTC) data, as shown in block 310.

Long term correlation for each incoming frame may be computed according to equation 1:

$$\text{LongTermCorrelation}_{Frame(i)}(t) = \text{SUM}_{over\ all\ pixels}(\text{Frame}(i) - \text{Frame}(t)) \quad \text{(eq. 1)}$$

Figure 4:
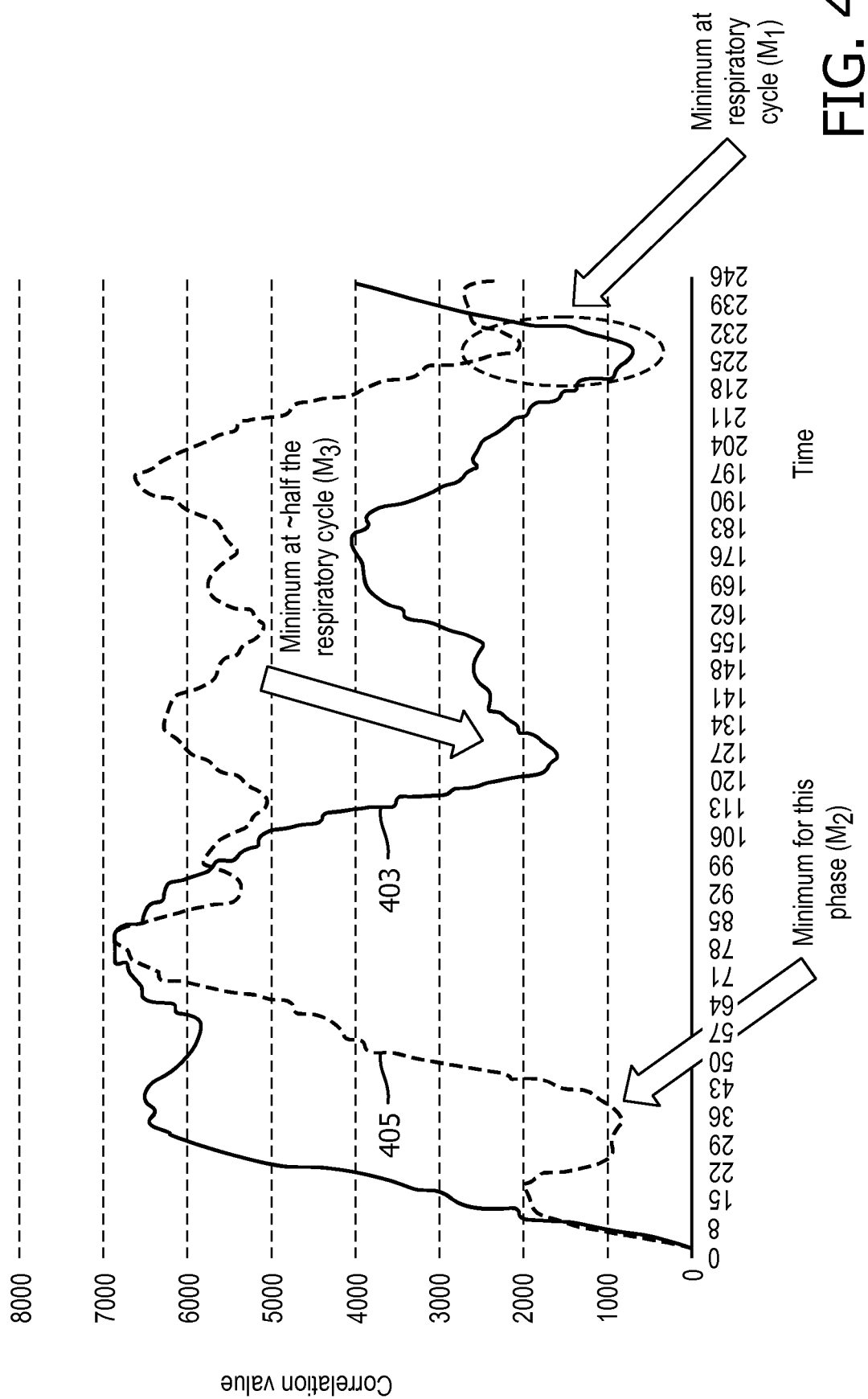
FIG. 4 shows long term correlation curves and local minima for determining parameters of a motion model in accordance with principles of the present disclosure.

Thus, a LTC curve for an incoming frame (Frame (i)) is generated by subtracting each of the previous frames (Frame (t)) from the incoming frame (or vice versa, by subtracting the incoming frame from the previous frames) and summing the result of the subtraction over all pixels. Preferably, the (temporally successive) frames from at least the previous one or two cycles are used to compute the LTC curve. FIG. 4 shows two example LTC curves, given in arbitrary units verses time, wherein the numbers on the abscissa indicate the number of the previous frame used in the subtraction. The LTC curve 403 in FIG. 4 corresponds to an LTC curve that was generated for an incoming frame at the position 507-I in the breathing cycle, as indicated in FIG. 5. The LTC curve 405 in FIG. 4 corresponds to an LTC curve that was generated for an incoming frame at the position 509-I in the breathing cycle, as indicated in FIG. 5.

In some examples, an LTC curve 311 may be generated for each incoming live frame. The cycle frequency and phase associated with a given live frame may be identified by determining local minima from the LTC data. For example, referring also to FIG. 4, which shows two LTC curves 403 and 405, the algorithm may look for at least two strong minima in each curve. The cycle frequency may be identified by looking for strong local minima $M_1$ at about the same location on each LTC curve. This minimum is caused by the fact that the breathing position—or displacement d(t)—one full cycle ago was similar to the displacement at present, and therefore the incoming frame is similar to the frame acquired one respiratory cycle ago, so that subtracting the frames from one another yields a minimum. The phase (or position in the respiratory cycle) associated with that particular image frame may be found by identifying another strong minima (e.g., $M_2$, $M_3$), relying also on a regularization principle—that is, that the phase of each new frame would be at a minima which would be consistent with the phase for the previous frame. In the example of FIGS. 4 and 5, curve 403 has a minimum at about half the respiratory cycle, which is an indication that the curve 403 corresponds to phase in the respiratory cycle which has an intermediate displacement d(t), like at position 507-I in FIG. 5. Thus, the respiratory movement was at the same position d(t) about half a cycle ago, causing a local minimum, and this gives an indication for the phase. For the curve 405, the second minimum $M_2$ is much closer to the origin of the LTC curve, indicating that this LTC curve corresponds to a position within the respiratory cycle which is closer to a peak displacement d(t) (such as maximum inhalation or maximum exhalation), e.g. to point 509_I in FIG. 5. The two LTC curves 403 and 405 in FIG. 4 are associated with frames distant in time, which is why the minima corresponding to the phase are spaced farther apart than may be the case for temporally consecutive frames.

Figure 6:
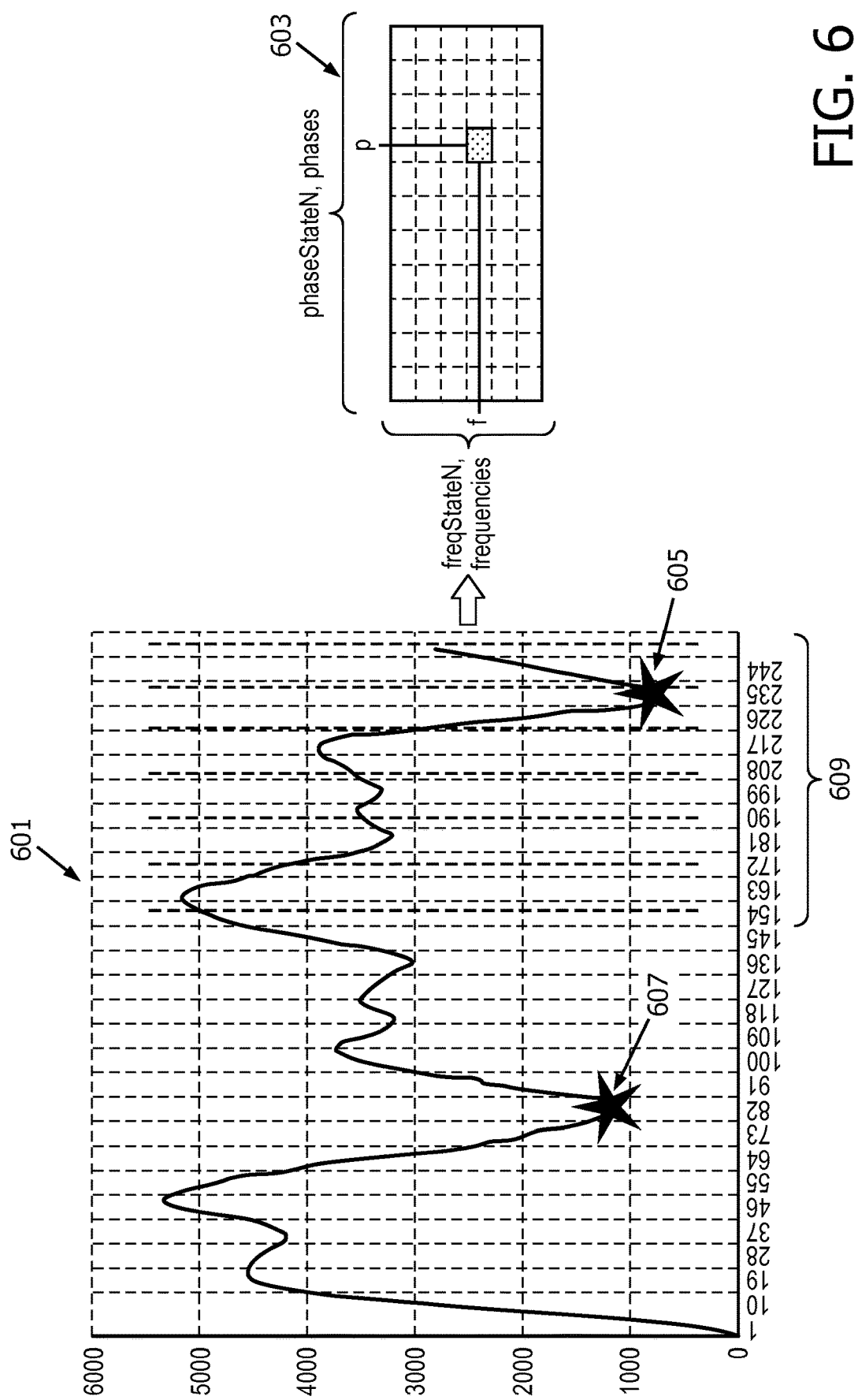
FIG. 6 illustrates mapping of long term correlation data to an error array for performing error minimization in accordance with principles of the present disclosure.

The algorithm in the example in FIG. 3 utilizes an error minimization technique to determine the relevant minima from the LTC data. For example, as shown in blocks 312, 314, and 318, using the LTC data obtained at block 310, costs (or errors) associated with each state from the number of states (stateN) are computed. This essentially provides a mapping of the LTC data to a M×N array 313 (e.g., freqStateN×phaseStateN), wherein M is the number of frequency states and N is the number of phase states. This M×N array 313 is also referred to as error array. This mapping may be performed using any known technique, for example by computing an area under the LTC curve for each increment for the number of frequency states for those frequencies within the set frequency range. In other words, and referring also to the example LTC curve 601 in FIG. 6, the frequency range 609, which may for example be between 3-5 seconds, is divided into equal increments of frequency states as indicated by the dashed lines. For clarity, to avoid cluttering the image, a small number (6 in this case) of frequency states are shown but it will be understood that a different number may be used, for example 30, 32, 36, etc. A similar process can be used for computing the error related to phase. For example, as phase is related to frequency, for any given frequency, the portion of the curve from time 0 to the time corresponding to the given frequency is divided into equal increments as the number of phase states and an area under the curve for each increment is computed thus obtaining the error values for the error array. FIG. 6 shows the minima 605 and 607 corresponding to the frequency and phase, respectively, associated with the live frame used to generate curve 601 and further shows an M×N error array 603 to which cost values for the curve 601 may be mapped, according to this example.

In some examples, cumulative costs for each state S from the number of states (stateN) may be computed to smooth the data, e.g., as shown in block 314, before the state associated with the minimum cost or error is selected, as shown in block 318. For example, the algorithm may be configured to assume that the respiratory rate stays stable over a fraction of cycle ("FractionOfCycle"), for example during one quarter ("Fraction"=4) of the respiratory cycle. Taking into account respective array of stateN errors associated with past frames, the algorithm may then compute the sum over this "FractionOfCycle", taking into account the variation of the phase by one "Fraction" and the duration of "FractionOfCycle" related with frequency state.

For each incoming frame, the algorithm outputs a respiratory rate (or frequency) within the set range and a phase, e.g., a value between 0-1, as shown in block 322, which may be selected based on the state with the minimum cost. The cost arrays computed at block 312 may also be provided to long term storage 316 e.g., to free up buffer space that may only be configured to temporarily store a subset of all the frames acquired over the time period of at least one motion cycle.

Figure 7:
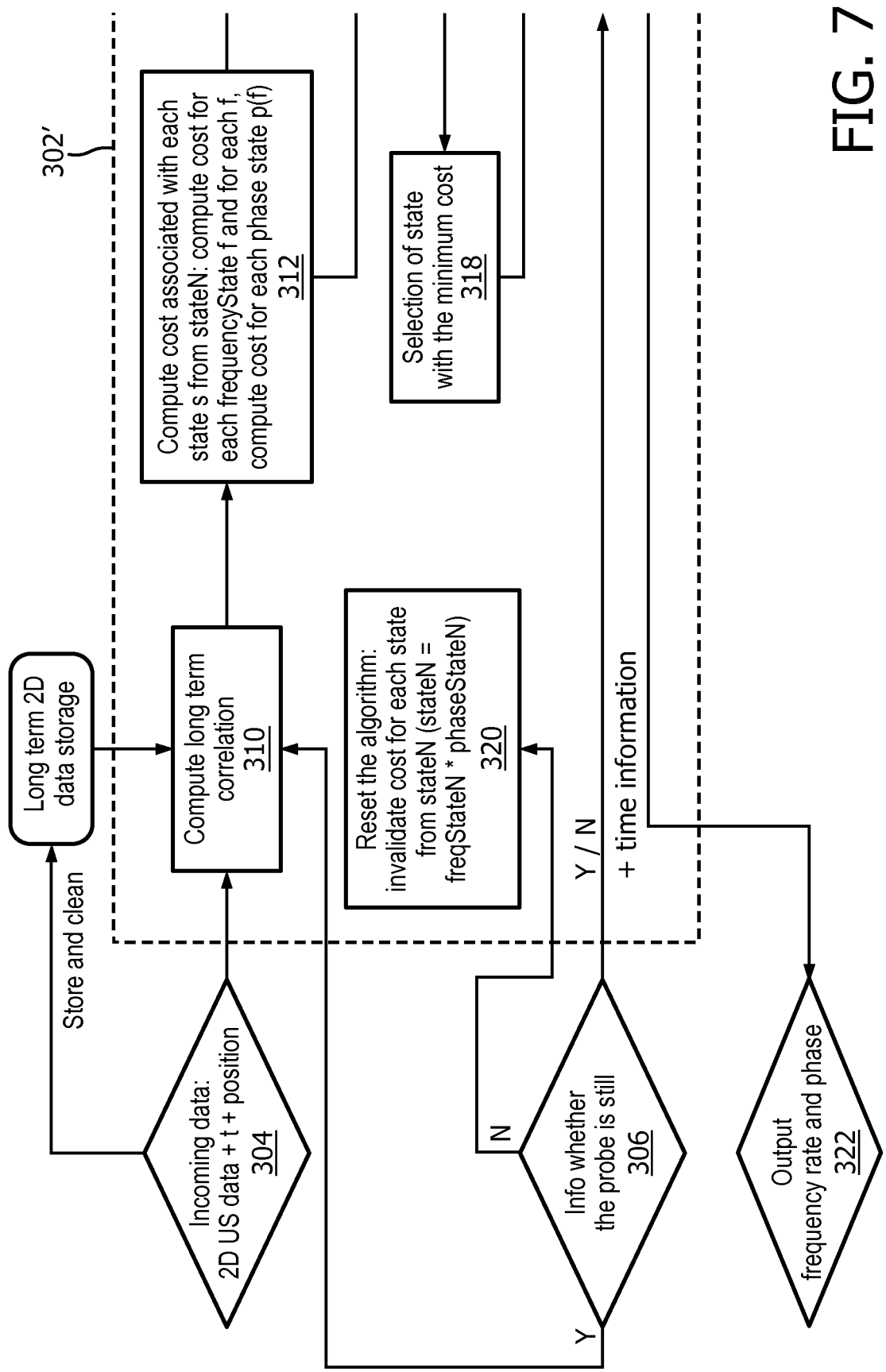
FIG. 7 shows a functional block diagram of an algorithm for correcting motion-induced misalignment, the algorithm including a static update block in accordance with principles of the present disclosure.

As described, the processor 302 may receive probe information, e.g., position information of the probe or an indication of whether the probe is stationary or moving (e.g., as shown in block 306). Upon a determination that the probe is moving, the synchronization of the phase and rate with each incoming frame may be paused (until the probe is again stationary), for example by resetting cost values as shown in block 320. In this situation, spatial registration between the live images and the pre-operative data may proceed using the version of the motion model from the last update without dynamic updates with each new frame. To that end, and referring also to FIG. 7, processor 302' may include a static update block 330. The probe information and timing information may additionally be coupled to the static update block 330. Responsive to an indication that the probe is moving, the static update block 330 may output a frequency which corresponds to a mean frequency over a period of time, as it will be expected that when the probe is moving the dynamic synchronization may not be reliable. As such, dynamic synchronization is paused and a mean frequency and next successive phase values are output at block 322 for each new frame while the probe is moving.

As show in the example in FIG. 5, a motion model may be defined, in the case of respiratory-induced liver motion, based on the rate, phase, and amplitude of the respiratory cycle for example according to equation 2:

motion model $d(t)$=amplitude*cos 2(rate*$t$+phase)  (eq. 2)

or according to equation 3:

motion model $d(t)$=amplitude*cos$^2$(rate*$t$+phase)  (eq. 32)

A motion model may be dynamically updated in the background for each live frame by the dynamic synchronization algorithm described with reference to FIG. 3, e.g., by obtaining an updated value, for each frame, for the rate and phase. The amplitude may be set responsive to user input or automatically set by the system such as based on motion estimation, e.g., as described further below with reference to the example in FIG. 8A, or based on a default value (e.g., about 20 mm) or range of optimized values, which may be further adjustable by user input. In a preferred embodiment, the frequency and phase of the motion model are derived from LTC curves, as described in detail above. The amplitude is automatically set by the system, e.g. based on a default value. In a preferred embodiment, the amplitude is further adjustable by user input, for example in case the combined image is visually not satisfactory.

Figure 8A:
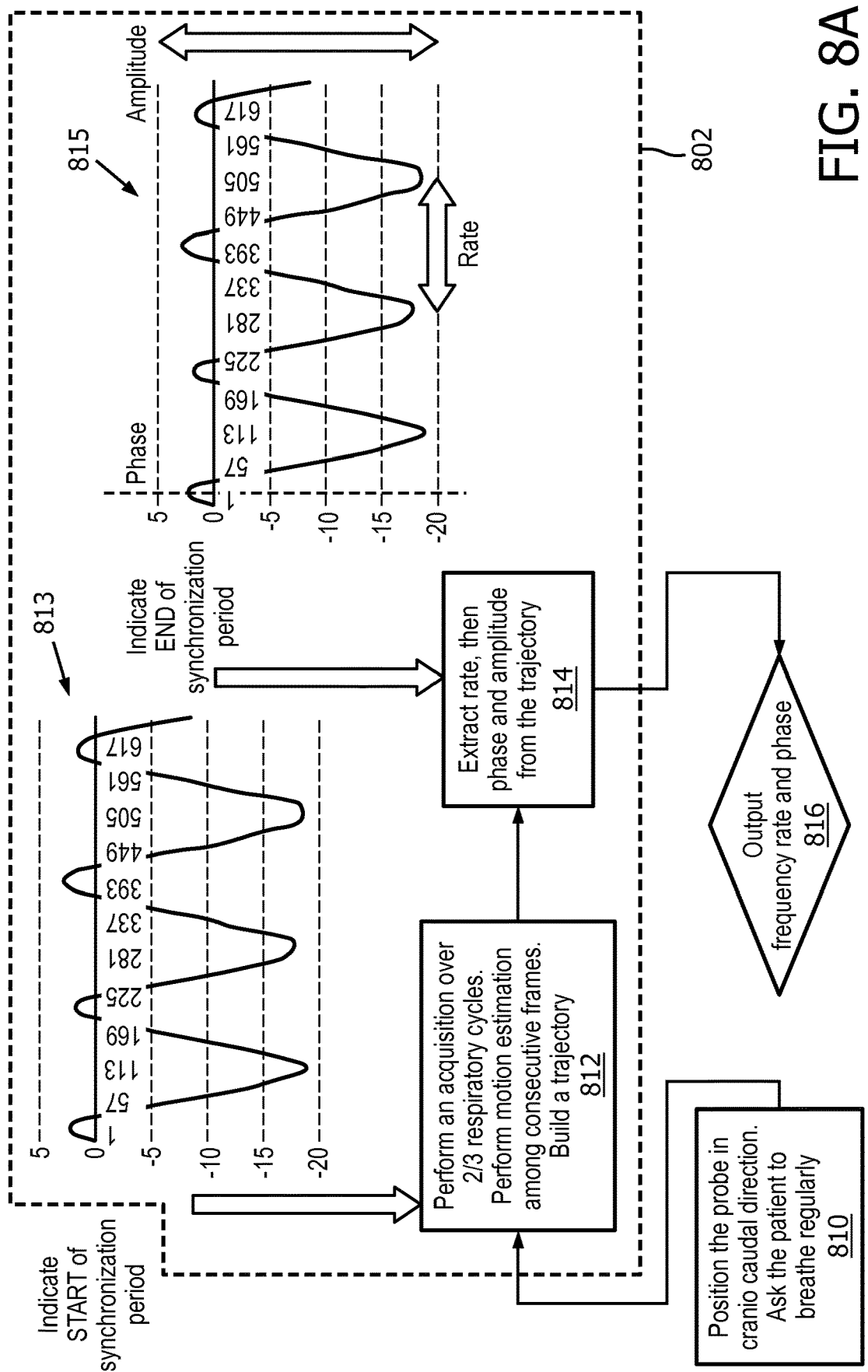
FIG. 8A shows a functional block diagram of another algorithm for correcting motion-induced misalignment when performing image fusion between real time and pre-operative data in accordance with further principles of the present disclosure.
Figure 8B:
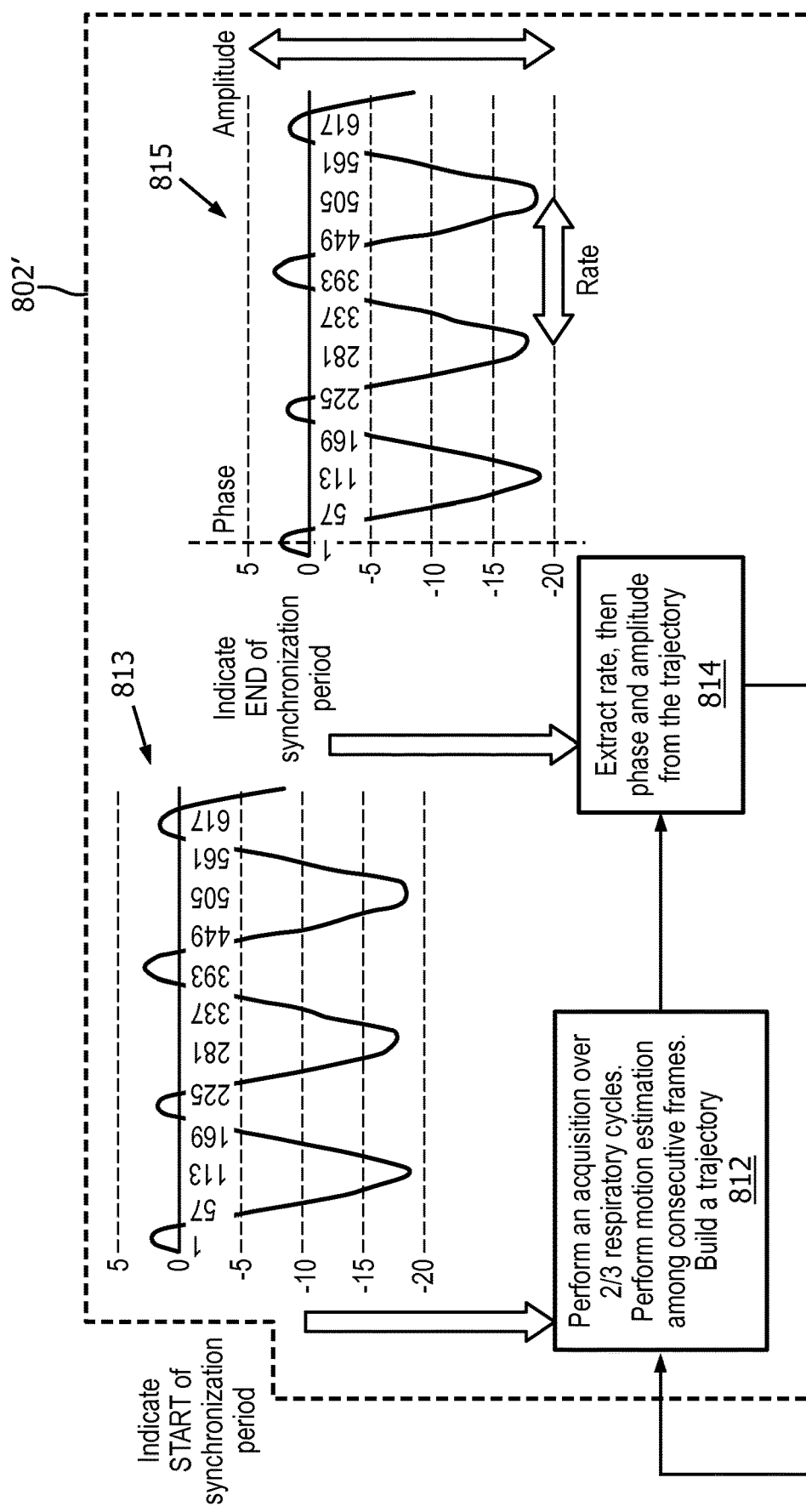
FIG. 8B shows a functional block diagram of the algorithm in FIG. 8A with the addition of a static update block in accordance with principles of the present disclosure.
Figure 8B:
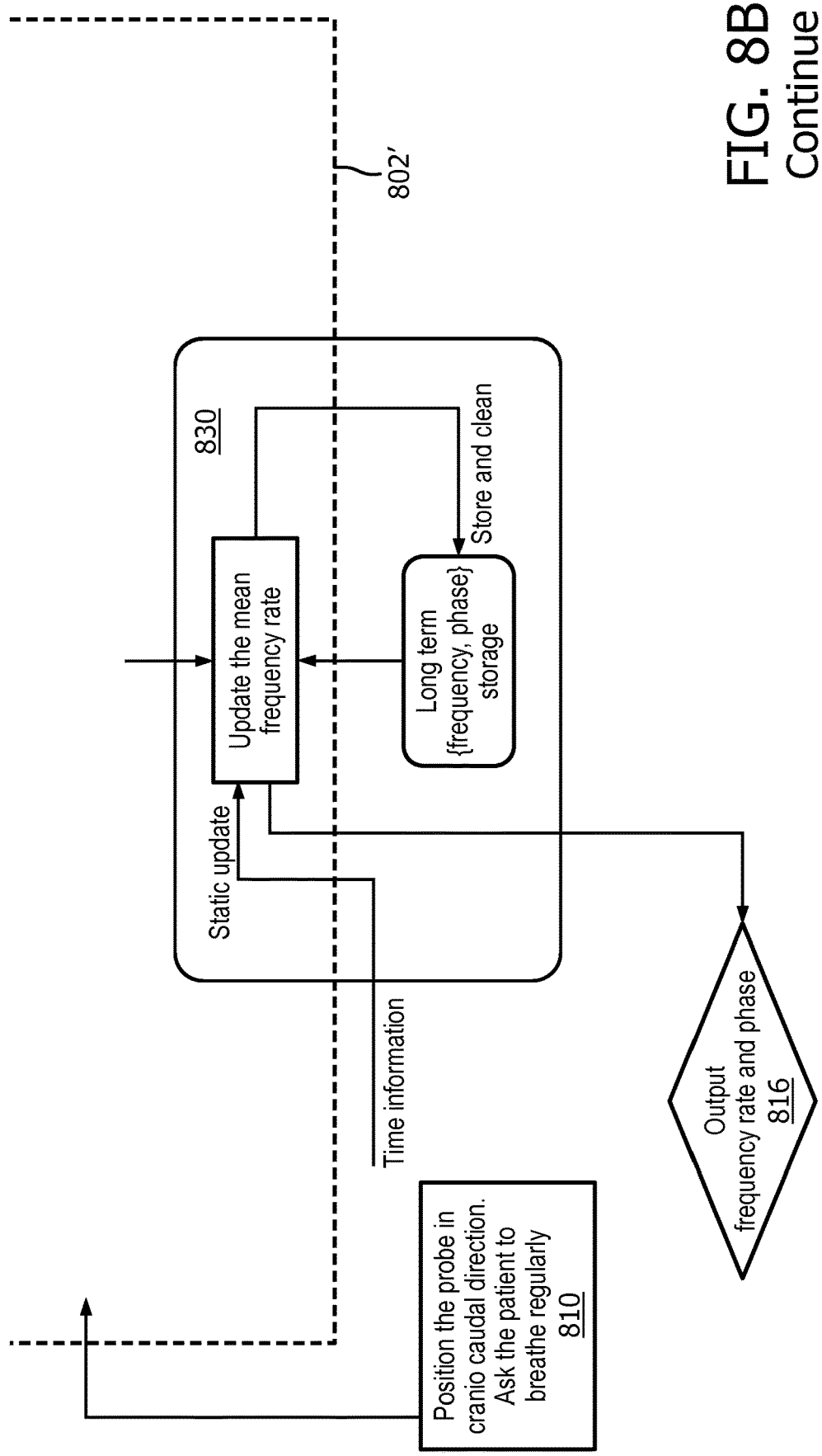

Referring now to FIGS. 8A and 8B, another technique for deriving or updating a motion model solely based on the ultrasound data (i.e., without reliance on the previously acquired image data) may utilize image processing performed on the ultrasound data to estimate the motion. The algorithms in the examples in FIGS. 8A and 8B rely on the ultrasound beam being aligned with the motion axis, e.g., the cranio-caudal direction in the case of respiratory motion, as shown in block 810. This can be achieved either manually, by positioning the probe such that the beam is aligned with the motion axis or by automatically steering the beam to obtain such alignment. In some case, e.g., when manual positioning is used, the system may provide feedback to the user to indicate when proper alignment has been obtained. In the examples in FIGS. 8A and 8B, synchronization (or model updating) is only performed responsive to user input. That is, the user may indicate to the system that re-synchronization is desired, for example by providing an indication of a start of a synchronization period. As shown in FIGS. 8A and 8B, the processor 802 receives an indication of a start of a synchronization period and an end of a synchronization period. The processor 802 performs image data acquisition over several respiratory cycles (2, 3, or more), as shown in block 812. The processor 802 performs motion estimation using the frames spanning the synchronization period, as shown in block 812. Motion estimation may be performed according to any currently known or later developed motion estimation technique such as using a block-matching motion estimation algorithm. A Block Matching Algorithm is a way of locating matching macroblocks in a sequence of frames for the purposes of motion estimation. For example, a block matching algorithm involves dividing the current frame of a sequence of frames into macroblocks and comparing each of the macroblocks with a corresponding block and its adjacent neighbors in a nearby frame (sometimes just the previous one). The output of the motion estimation is an estimated trajectory of the motion, as shown at 813. The trajectory is provided to block 814 where rate, phase and amplitude of the motion may be extracted from the estimated trajectory, as shown by 815. One way to obtain the rate, phase and amplitude from the trajectory is to search for the pair {phase, rate} such that:

(phase,rate)=arg max(sum(abs($C$[phase+$k$*rate]−$C$ [phase+($k$+1)*rate]))/($k$ max+1)

The sum is computed as long as the value of [phase +(k+1)*rate] exists in the curve, hence k max is the last possible k value. The maximum argument provides the amplitude. Other techniques may be used to obtain the rate, phase, and amplitude. The rate (or frequency), phase, and amplitude are output as shown in block 816 and used to identify motion-compensated image planes from the pre-operative data for fusion with the real-time frames. The processor 802' in FIG. 8B is similar to processor 802 but differs in that it includes a static update block 830 similar to the static update block of the example in FIG. 7.

Figure 9:
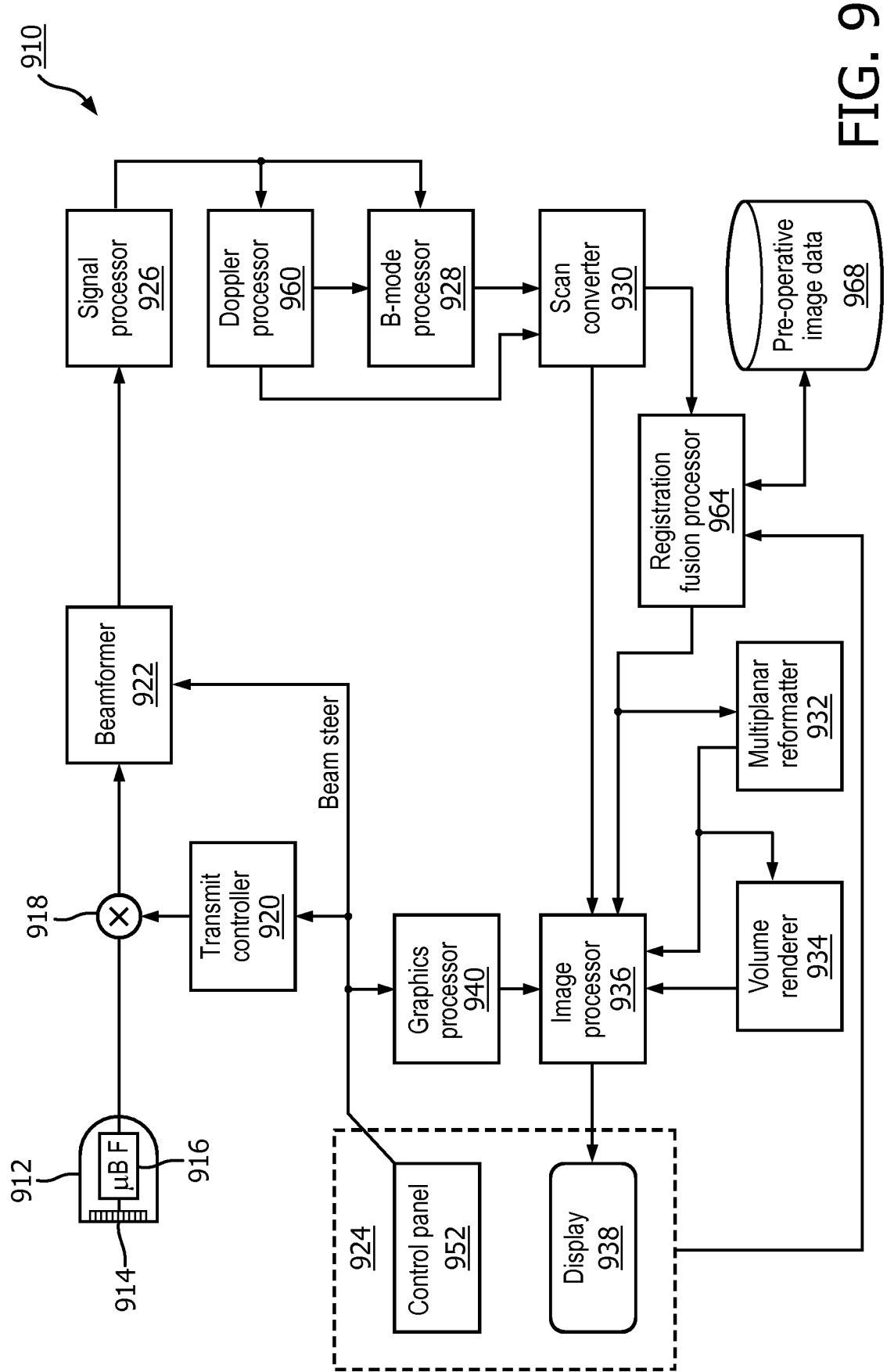
FIG. 9 shows a block diagram of an ultrasound imaging system in accordance with principles of the present disclosure.

FIG. 9 shows a block diagram of an ultrasound imaging system constructed in accordance with the principles of the present disclosure. Some or all of the components of ultrasound imaging system 910 may be used to implement ultrasound imaging systems in accordance with any of the examples herein, for example system 100 in FIG. 1. The ultrasound imaging system 910 in FIG. 9 includes ultrasound probe 912, transducer array 914, beamformer 922 and optionally microbeamformer 916, transmit/receive (T/R) switch 918, transmit controller 920, and one or more processing components for generating ultrasound images from detected echoes. For example, the system 910 may include signal processor 926, B-mode processor 928, Doppler processor 960, scan converter 930, multiplanar reformatter 932, volume renderer 934, image processor 936, graphics processor 940, and others. The system may also include user interface 924, input device 952, and output device 938. The components shown in FIG. 9 are merely illustrative, and other variations, including eliminating components, combining components, rearranging components, and substituting components are all contemplated.

As shown, the ultrasound imaging system 910 includes an ultrasound probe 912, which includes a transducer array 914 for transmitting ultrasound waves and receiving echo information. A variety of transducer arrays may be used, e.g., linear arrays, curved arrays, or phased arrays. The transducer array 914, for example, can include a two dimensional array (as shown) of transducer elements capable of scanning in both elevation and azimuth dimensions for 2D and/or 3D imaging. The transducer array 914 may be coupled to a microbeamformer 916, which may be located in the ultrasound probe 112. The microbeamformer 916 controls transmission and reception of signals by the transducer elements in the array 914. In the illustrated example, the microbeamformer 916 is coupled to a transmit/receive (T/R) switch 918, which switches between transmission and reception and protects the main beamformer 922 from high energy transmit signals. In some embodiments, for example in portable ultrasound systems, the T/R switch 918 and other elements in the system can be included in the ultrasound probe 912 rather than in a separate ultrasound system base. The ultrasound system base typically includes software and hardware components including circuitry for signal processing and image data generation as well as executable instructions for providing a user interface.

The transmission of ultrasonic pulses from the transducer array 914 under control of the microbeamformer 916 is directed by the transmit controller 920 coupled to the T/R switch 918 and the beamformer 922, which may receive input from the user's operation of a user interface 924. The user interface 924 may include one or more input devices such as a control panel 952, which may include one or more mechanical controls (e.g., buttons, encoders, etc.), touch sensitive controls (e.g., a trackpad, a touchscreen, or the like), and other known input devices. The user interface 924 may include one or more output device, e.g., a display 938 configured to display images (e.g., fused images of real time and pre-operative data). Another function which may be controlled by the transmit controller 920 is the direction in which beams are steered. Beams may be steered straight ahead from (orthogonal to) the transducer array 914, or at different angles for a wider field of view. The partially beamformed signals produced by the microbeamformer 916 are coupled to a main beamformer 922 where partially beamformed signals from individual patches of transducer elements are combined into a fully beamformed signal. The beamformed signals are coupled to a signal processor 926.

The signal processor 926 can process the received echo signals in various ways, such as bandpass filtering, decimation, I and Q component separation, and harmonic signal separation. The signal processor 126 may also perform additional signal enhancement such as speckle reduction, signal compounding, and noise elimination. The processed signals may be coupled to a B-mode processor 928 for producing B-mode image data. The B-mode processor can employ amplitude detection for the imaging of structures in the body. The signals produced by the B-mode processor 928 may be coupled to a scan converter 930 and a multiplanar reformatter 932. The scan converter 930 is configured to arrange the echo signals in the spatial relationship from which they were received in a desired image format. For instance, the scan converter 930 may arrange the echo signal into a two dimensional (2D) sector-shaped format, or a pyramidal or otherwise shaped three dimensional (3D) format. The multiplanar reformatter 932 can convert echoes which are received from points in a common plane in a volumetric region of the body into an ultrasonic image (e.g., a B-mode image) of that plane, for example as described in U.S. Pat. No. 6,443,896 (Detmer). A volume renderer 934 may generate an image of the 3D dataset as viewed from a given reference point, e.g., as described in U.S. Pat. No. 6,530,885 (Entrekin et al.).

The system 910 may also include a Doppler processor 960. The signals from the signal processor 926 may be coupled to a Doppler processor 960, which may be configured to estimate the Doppler shift and generate Doppler image data. The Doppler image data may include color data, which may be overlaid with B-mode (or grayscale) image data for display. The Doppler processor 960 may be configured to estimate velocity and power in accordance with known techniques. For example, the Doppler processor may include a Doppler estimator such as an auto-correlator, in which velocity (Doppler frequency) estimation is based on the argument of the lag-one autocorrelation function and Doppler power estimation is based on the magnitude of the lag-zero autocorrelation function. Motion can also be estimated by known phase-domain (for example, parametric frequency estimators such as MUSIC, ESPRIT, etc.) or time-domain (for example, cross-correlation) signal processing techniques. Other estimators related to the temporal or spatial distributions of velocity such as estimators of acceleration or temporal and/or spatial velocity derivatives can be used instead of or in addition to velocity estimators.

Output (e.g., images) from the scan converter 930, the multiplanar reformatter 932, and/or the volume renderer 934 may be coupled to an image processor 936 for further enhancement, buffering and temporary storage before being displayed on an image display 938. In some embodiments, for example, when performing image fusion of 2D real-time ultrasound data with pre-operative image data, the system may include or be communicatively coupled to a source of pre-operative data 968. The 2D images form the scan converter 930 may first be passed through a registration and fusion processor 964 which may be configured to correct for motion-induced misalignment in real-time prior to fusing and sending the combined images downstream, e.g., to the image processor and/or graphics processor. A graphics processor 940 may generate graphic overlays for display with the images. These graphic overlays can contain, e.g., standard identifying information such as patient name, date and time of the image, imaging parameters, and the like. For these purposes, the graphics processor may be configured to receive input from the user interface 924, such as a typed patient name or other annotations. In some embodiments, the system 100 may be configured to receive user input via the user interface 924 for setting parameters of the algorithms described herein. In some embodiments, one or more functions of at least one of the graphics processor, image processor, volume renderer, and multiplanar reformatter may be combined into an integrated image processing circuitry (the operations of which may be divided among multiple processor operating in parallel) rather than the specific functions described with reference to each of these components being performed by a discrete processing unit. Furthermore, while processing of the echo signals, e.g., for purposes of generating B-mode images or Doppler images are discussed with reference to a B-mode processor and a Doppler processor, it will be understood that the functions of these processors may be integrated into a single processor.

Figure 10:
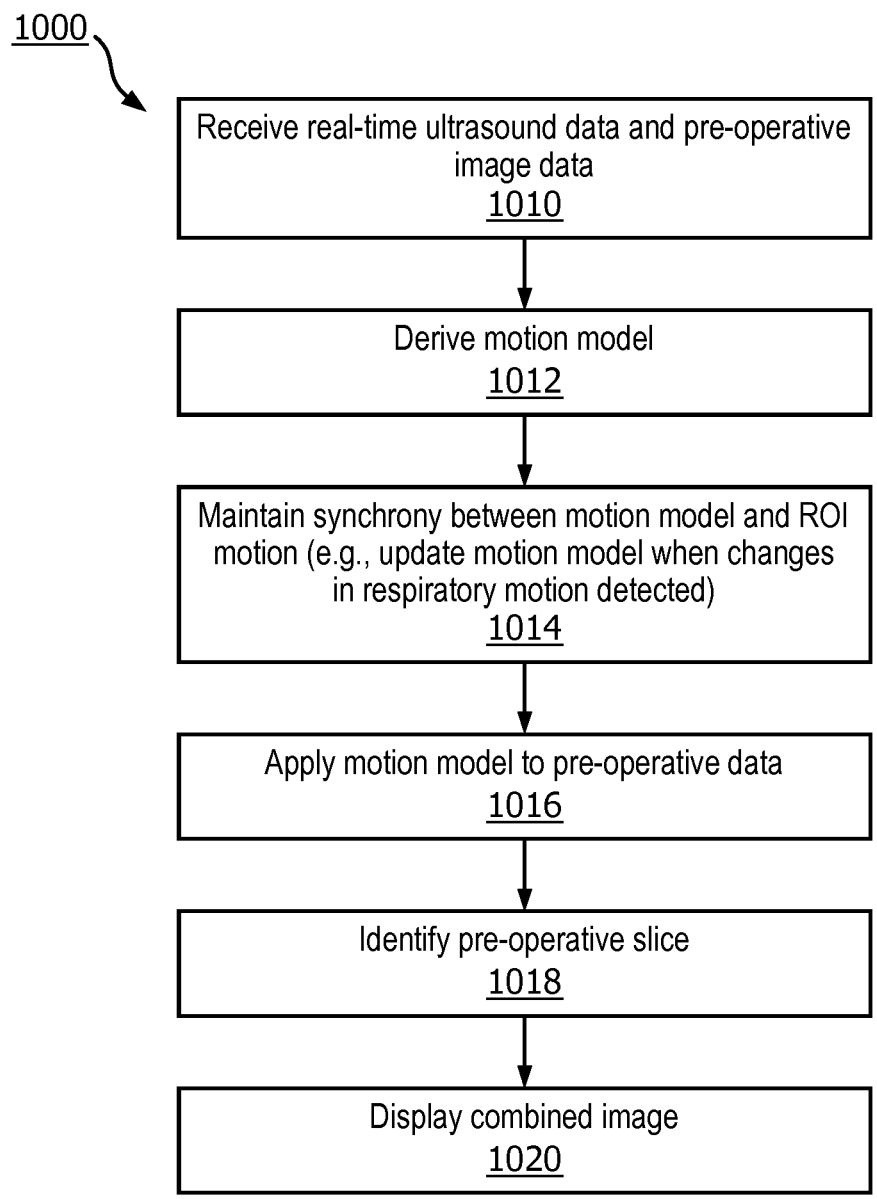
FIG. 10 is a flow diagram of a method for real time imaging in accordance with principles of the present disclosure.

FIG. 10 shows a flow diagram of a method 1000 according to principles of the present disclosure. The method may include receiving real-time ultrasound image data as shown in block and pre-operative image data (e.g., CT or MRI data) as shown in block 1010. Real-time ultrasound images may be generated for each incoming frame and spatially registered with the preoperative data for image fusion. Spatial registration according to the principles of the present disclosure may involve spatially aligning the real-time images with pre-operative data based on position data and further correcting for motion-induced misalignment. To that end, the method 1000 may include deriving a motion model based on the real-time ultrasound image data, as shown in block 1012. The motion model may be used to correct for the motion-induced misalignment by allowing the system to automatically select a motion-compensated image plane. The method may further involve dynamically updating the motion model, e.g., to maintain synchrony between the motion model and the organ motion, as shown in block 1014. The motion model 1016 may be applied to the pre-operative data as shown in block 1016 to identify a motion-compensated preoperative slice for fusion with the real time image data as shown in block 1018 and the combined image may then be provided on a display 1020. Methods according to the examples herein may include any combination of the steps or functions performed by or associated with execution of the algorithms described herein.

In view of this disclosure it is noted that the various methods and devices described herein can be implemented in hardware, software and firmware. Further, the various methods and parameters are included by way of example only and not in any limiting sense. In view of this disclosure, those of ordinary skill in the art can implement the present teachings in determining their own techniques and needed equipment to affect these techniques, while remaining within the scope of the disclosure. The functionality of one or more of the processors described herein may be incorporated into a fewer number or a single processing unit (e.g., a CPU or a GPU) or, alternatively, they may be distributed among a greater number of processing units, and may be implemented using application specific integrated circuits (ASICs) or general purpose processing circuits which are programmed responsive to executable instruction to perform the functions described herein. A computer program (e.g., executable instructions) may be stored/distributed on any suitable computer-readable medium, such as an optical storage medium or a solid-state medium supplied together with or as part of other hardware, but may also be distributed in other forms, such as via the Internet or other wired or wireless telecommunication systems.

It will be understood that any one of the examples, embodiments or processes described herein may be combined with one or more other examples, embodiments and/or processes or be separated and/or performed amongst separate devices or device portions in accordance with the present systems, devices and methods. Finally, the above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

The invention claimed is:

1. An ultrasound imaging system operatively associated with an ultrasound probe for imaging a subject in real time and with a position-tracking sensor connected to the probe, the system comprising:
 a processor communicatively coupled to the ultrasound probe and to a source of previously-acquired image data, wherein the previously-acquired image data comprises a 3D dataset corresponding to an imaged volume of the subject, and wherein the processor is configured to:
 receive real-time ultrasound image data;
 generate a real-time ultrasound image based on a current image frame from the real-time ultrasound data;
 derive a motion model comprising a displacement function of a position within an anatomical feature of the subject as a function of time from the real-time ultrasound image data, the displacement function having a plurality of parameters that are extracted from the real-time ultrasound data;
 generate long term correlation (LTC) data for each of a plurality of incoming frames of the real-time ultrasound image data from the real-time ultrasound image data received over a time period greater than one motion cycle, wherein generating each data point of the LTC data comprises subtracting an incoming frame of the plurality of frames from previously received ones of the plurality of incoming frames and summing a result of the subtraction over all pixels of the incoming frame of the plurality of incoming frames;
 determine a cycle frequency and a phase of a motion of the anatomical feature associated with each incoming frame by identifying at least two local minima of a LTC curve corresponding to the LTC data associated with each incoming frame, wherein the cycle frequency and the phase are included in the plurality of parameters of the displacement function;

resynchronize the motion model to movement the motion of the anatomical feature of the subject based on position information from the position-tracking sensor;

spatially register the real-time ultrasound image to the previously-acquired image data based on the position information from the position-tracking sensor and the motion model for motion-compensating the previously-acquired image data; and fuse the real-time ultrasound image with the motion-compensated previously-acquired image data to produce a combined image.

2. The ultrasound imaging system of claim 1, wherein the motion model is defined based, at least in part, on the cycle frequency, the phase, and an amplitude of the motion of the anatomical feature in the imaged volume, and wherein the processor is configured to determine the cycle frequency, the phase, the amplitude, or a combination thereof from the real-time ultrasound image data received over the time period greater than one motion cycle.

3. The ultrasound imaging system of claim 1, wherein the processor is further configured to perform error minimization on the LTC data to dynamically resynchronize the motion model.

4. The ultrasound imaging system of claim 1, wherein the processor is configured to determine whether the ultrasound probe is stationary based on the position information from the position-tracking sensor, and to dynamically update the motion model only when the ultrasound probe is determined to be stationary.

5. The ultrasound imaging system of claim 1, wherein the processor is configured to derive the motion model by performing motion estimation on successive image frames of the real time data received over a period equal to or greater than at least two motion cycles.

6. The ultrasound imaging system of claim 1, wherein the processor is further configured to receive user input indicative of a start and an end of a synchronization period, and wherein the processor is configured to perform motion estimation on image frames received over the synchronization period.

7. The ultrasound imaging system of claim 1, wherein the motion model is configured to estimate a respiratory-induced motion of the anatomical feature along a craniocaudal direction of the subject as a function of time based on breathing rate, phase and amplitude of the respiratory motion of the subject.

8. The ultrasound imaging system of claim 1, wherein the previously-acquired image data comprises 3D dataset acquired using magnetic resonance (MR), computed tomography (CT), or ultrasound (US) imaging.

9. The ultrasound imaging system of claim 1, further comprising a display unit, and wherein the processor is configured to cause the combined image to be displayed on the display unit in real time.

10. A method of imaging comprising:

receiving real-time ultrasound image data responsive to ultrasound transmitted by a probe toward a subject, wherein the probe is associated with a position-tracking sensor;

generating a real-time ultrasound image based on a current image frame from the real-time ultrasound data;

deriving a motion model comprising a displacement function as a function of time from the real-time ultrasound image data, wherein the motion model is defined based, at least in part, on a cycle frequency, a phase, and an amplitude of a motion of the anatomical feature in the imaged volume, wherein the deriving a motion model from the real-time ultra sound image data comprises determining the cycle frequency, the phase, the amplitude, or a combination thereof from the real-time ultrasound image data received over a time period greater than one motion cycle;

generating long term correlation (LTC) data for each of a plurality of incoming frames of the real-time ultrasound image data received over a time period greater than one motion cycle, wherein each data point of the LTC data comprises a sum over all pixels of an incoming frame of the plurality of incoming frames subtracted from previously received ones of the plurality of incoming frames;

determining the cycle frequency and the phase associated with each incoming frame based on local minima of LTC curves corresponding to the LTC data associated with each incoming frame:

resynchronizing the motion model to the motion of an anatomical feature of the subject based on position information from the position-tracking sensor;

accessing a previously-acquired image data set corresponding to an imaged volume of the subject, spatially registering the real-time ultrasound image to the previously-acquired image data set based on position information from the position-tracking sensor and the motion model for motion-compensating the previously-acquired image data set; and fusing the real-time ultrasound image with the motion-compensated previously-acquired image data set to produce a combined image.

11. The method of claim 10, wherein the method further comprises:

performing error minimization on the LTC data to dynamically resynchronize the motion model; and detecting movement of the probe and pausing resynchronization of the motion model responsive to detected movement of the probe.

12. A non-transitory computer-readable medium comprising processor-executable instructions, which when executed by one or more processors of a medical imaging system cause the one or more processors to perform a method according to claim 10.

13. The method of claim 11, further comprising maintaining registration between the real-time image frames and the previously-acquired image data during a period associated with movement of the probe based on a version of the motion model prior to the detected movement of the probe.

* * * * *